(12) United States Patent
Michels

(10) Patent No.: US 9,545,347 B1
(45) Date of Patent: Jan. 17, 2017

(54) MEDICAL AMBULATORY DEVICE FOR CHILDREN AND METHOD OF USE

(71) Applicant: Elizabeth Michels, Aliquippa, PA (US)

(72) Inventor: Elizabeth Michels, Aliquippa, PA (US)

( * ) Notice: Subject to any disclaimer, the term of this patent is extended or adjusted under 35 U.S.C. 154(b) by 0 days.

(21) Appl. No.: 14/970,786

(22) Filed: Dec. 16, 2015

(51) Int. Cl.
| | |
|---|---|
| *B62B 1/00* | (2006.01) |
| *A61G 5/02* | (2006.01) |
| *A61G 5/12* | (2006.01) |
| *A61G 5/10* | (2006.01) |
| *B62K 9/02* | (2006.01) |
| *B62K 5/023* | (2013.01) |
| *B62K 5/08* | (2006.01) |

(52) U.S. Cl.
CPC ............... *A61G 5/02* (2013.01); *A61G 5/1059* (2013.01); *A61G 5/12* (2013.01); *B62K 5/023* (2013.01); *B62K 5/08* (2013.01); *B62K 9/02* (2013.01); *A61G 2005/1051* (2013.01); *A61G 2005/125* (2013.01); *A61G 2005/127* (2013.01)

(58) Field of Classification Search
CPC ............ B62K 5/02; B62K 5/023; B62K 5/08; A61G 5/1059; A61G 5/12
See application file for complete search history.

(56) References Cited

U.S. PATENT DOCUMENTS

| | | | | |
|---|---|---|---|---|
| 4,095,816 A | * | 6/1978 | Langieri | B62K 9/00 280/87.021 |
| 6,676,118 B2 | * | 1/2004 | Chou | F16F 1/128 267/175 |
| 2007/0238585 A1 | * | 10/2007 | Mondello | A63B 69/16 482/57 |

* cited by examiner

*Primary Examiner* — John Walters
*Assistant Examiner* — James Triggs
(74) *Attorney, Agent, or Firm* — Acker Wood IP Law, LLC; Gwen R. Acker Wood

(57) ABSTRACT

The present invention provides a medical ambulatory device and method comprised of an ambulatory vehicle and a flexible, elastic harness attached to the vehicle for suspending an injured lower limb of a child in a substantially elevated position in order to maintain mobility of the child, encourage movement, and provide ample exercise and fun for the child while the injury is healing.

20 Claims, 7 Drawing Sheets

MEDICAL AMBULATORY DEVICE FOR CHILDREN AND METHOD OF USE

FIELD OF THE INVENTION

The present invention relates to medical ambulatory devices and, in particular, to a medical ambulatory device and method of use for a child with an injured lower limb, such as a broken bone that requires a cast, which allows the child to have mobility and encourages exercise.

BACKGROUND OF THE INVENTION

Approximately one-third of all children suffer at least one bone fracture before the age of 17. Children who have a broken leg, ankle or foot, or cannot bend their knee because of a cast, still want to move and explore their world, and are likely to remain as active as possible. However, children who are placed in a wheel chair or provided with a walker, depending on the age of the child, typically will be unable to physically move themselves in the wheel chair and have difficulty using the walker. This results in a care-giver having to hold the child in many situations, which can be difficult and uncomfortable, and can cause physical problems in the care-giver, such as back problems. Thus, because of the lack of adequate ambulatory options for children with a broken leg, ankle or foot, many of them end up experiencing decreased activity which can causes an overall decrease in muscle and bone mass and strength.

There exists a need therefore, for an ambulatory device for children with a broken leg, ankle or foot to stay mobile without the help of others and that encourages movement and exercise so that optimal muscle and bone mass and strength are maintained.

SUMMARY OF THE INVENTION

The present invention fulfills this need by providing a medical ambulatory device and method of use which allows a child with an injured lower limb, such as a broken bone in the leg, ankle or foot that may require a cast, to maintain mobility, which encourages movement, and which provides ample exercise and fun for the child while healing the injury.

In particular, the present invention provides medical ambulatory device for children, comprised of a flexible, elastic, harness, the harness having a first end and second end, the first end having a harness attachment means, the second end terminating in a circular ring having an interior opening, the circular ring capable of expanding or contracting to fit securely around an injured limb of a child; a counterbalance weight; and an ambulation vehicle, comprised of a handlebar having two ends and a central portion; a seat having a front end, a back end, a top side, a bottom side, a first side and a second side, the front end having a circular opening therein, and the bottom side having two sets of a first support bracket attachment means, a second support bracket attachment means and a third support bracket attachment means, a first set located adjacent to the first side of the seat, and a second set located adjacent to the second side of the seat, the first, second and third support bracket attachment means spaced evenly apart; a wheel baseboard having a front end, a back end, a first side, a second side and a central portion, the front end having a circular opening therein; a first adjustable seat support bracket and a second adjustable seat support bracket, each adjustable seat support bracket having a first end and a second end, the first end of said first adjustable seat support bracket reversibly attached to the first, second or third attachment mean of the first set, and the second end of said first adjustable seat support bracket connected to the central portion and adjacent to the first side of the wheel baseboard, and the first end of the second adjustable seat support bracket is reversibly attached to the first, second or third support bracket attachment mean of the second set, and the second end of the second adjustable seat support bracket connected to the central portion and adjacent to second side of the wheel baseboard; a first front wheel and a second front wheel connected to a wheelbase located at the front end of the wheel baseboard, the wheelbase adjustable in width; a back wheel located on the back end of the wheel baseboard; an adjustable vertical pole having a first end and second end, the adjustable vertical pole comprised of two pole parts in which one pole part fits telescopically into the other pole part so that the length of the adjustable vertical pole can be increased or decreased, the first end of the adjustable vertical pole connected to the central portion of the handlebar, the second end of the adjustable vertical pole fitting into the seat circular opening and the wheel baseboard circular opening, wherein the harness attachment means is attached adjacent to the one end of the handlebar, and wherein the counterbalance weight is attached adjacent to the other end of the handlebar.

The present invention further provides a method of ambulation for a child having an injured leg, ankle or foot, the method comprising having a child use the above-described medical ambulatory device by: adjusting the height of the handlebar and seat of the ambulation vehicle to a height that is substantially the height that is eye-level of the child when the child is standing; adjusting the width of the wheelbase to provide optimal stability; placing the flexible, elastic ring-shaped harness on the side of the handlebar that is the same side of the injured lower limb of the child, and placing the counterbalance weight on the other side of the handlebar; placing the child on the seat of the ambulation vehicle; having the child grasp the handlebar with their hands; placing the foot of the injured limb of the child through the harness so that the injured lower limb is suspended in the air in a substantially elevated position; and moving the ambulation vehicle by having the child repeatedly push back on the ground with their uninjured lower limb in order to propel the ambulation vehicle forward.

BRIEF DESCRIPTION OF THE DRAWINGS

A fuller understanding of the invention can be gained from the following description when read in conjunction with the accompanying figures, where like reference numerals refer to identical or functionally similar elements throughout the separate views, which illustrate some, but not the only and exclusive, examples of embodiments of the invention and, as such, the figures disclosed herein are to be considered illustrative rather than limiting. In the drawings.

DETAILED DESCRIPTION OF THE INVENTION

Figure 1:
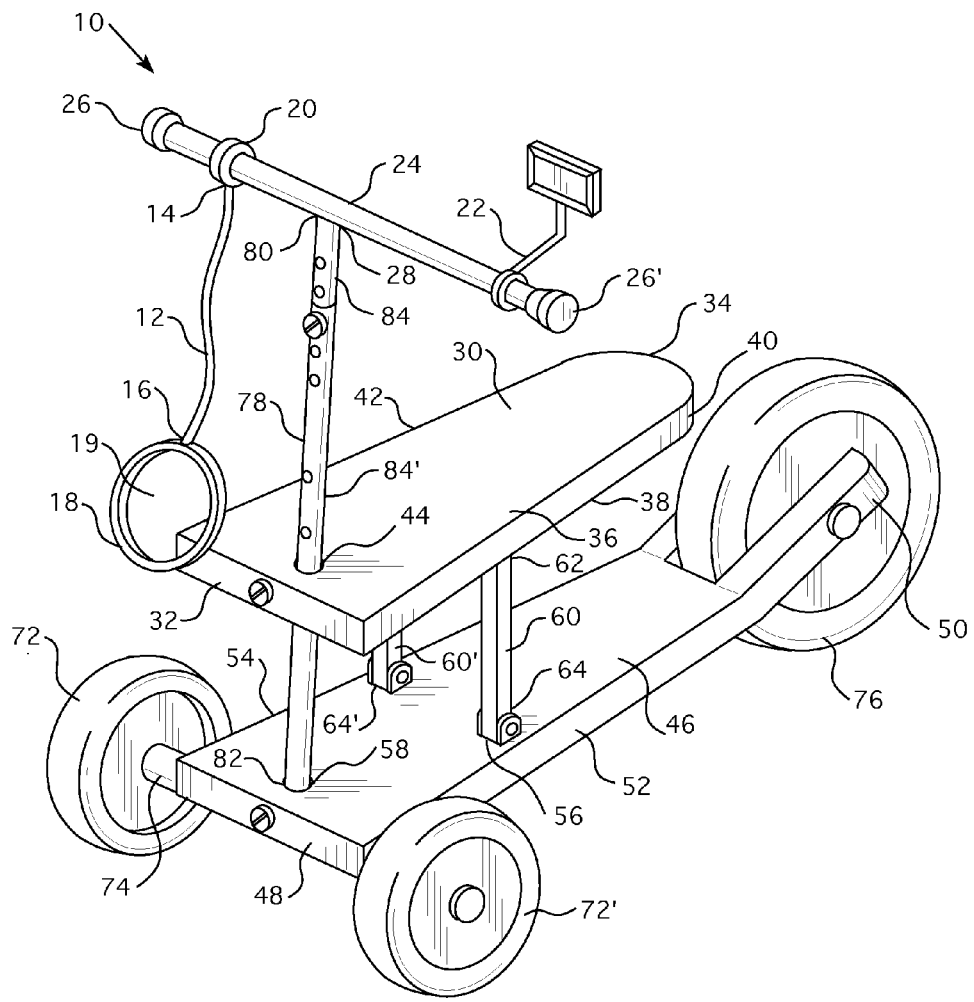
FIG. 1 is a perspective view of the medical ambulatory device, in accordance with an embodiment of the invention.

The present invention provides a device and method for a child with a lower limb injury, such as a broken leg, ankle or foot that may be in a cast, to ambulate freely, easily, safely, and with much enjoyment. A surprising feature of the ambulatory device and method of the present invention is its ability to suspend an injured lower limb in the air substantially in an elevated position, which allows the injured lower limb to heal quickly and effectively due to its elevation and lack of pressure points at any one area of the lower limb, while at the same time providing a safe and effective ambulatory device while an injury is healing. Further, the ambulatory device of the present invention allows a child to experience easy mobility and encourages exercise, which aids circulation, and thus is advantageous during the healing process. Caregivers of children with injured or broken bones are all too aware of the difficulty in getting children to move effectively, as children find it very hard to use crutches and walkers. In addition, because children typically have a very high energy level, the ambulatory device of the present invention provides a safe and effective outlet for energy expenditure without the risk of further injury.

Referring now to FIGS. 1-7, the medical ambulatory device 10 includes an ambulation vehicle comprised of a handlebar 24 having two ends 26, 26' and a central portion 28 (shown in FIGS. 1-3 and 7); a seat 30 having a front end 32, a back end 34, a top side 36, a bottom side 38, a first side 40 and a second side 42, the front end having a circular opening 44 therein (shown in FIG. 1); and the bottom side 38 having two sets of a first support bracket attachment means 66, 66', a second support bracket attachment means 68, 68' and a third support bracket attachment means 70, 70' (shown in FIG. 3); a wheel baseboard 46 having a front end 48, a back end 50, a first side 52, a second side 54 and a central portion 56, the front end 48 having a circular opening 58 therein (shown in FIG. 1); a first adjustable seat support bracket 60 and a second adjustable seat support bracket 60', each adjustable seat support bracket 60, 60' having a first end 62 62' and a second end 64 64'(shown in FIGS. 1 and 2), the first end 62 of the first adjustable seat support bracket 60 reversibly attached to the first set of the first 66, second 68 or third support attachment means 70, and the second end 64 of the first adjustable seat support bracket 60 connected to the central portion 56 and adjacent to the first side 52 of the wheel baseboard 46, and said first end of said second adjustable seat support bracket is reversibly attached to the second set of the first 66', second 68' or third attachment means 70', and said second end of said second adjustable seat support bracket connected to the central portion and adjacent to the second side of the wheel baseboard (shown in FIGS. 4-6); a first front wheel 72 and a second front wheel 72' connected to a wheelbase 74 located at the front end 48 of the wheel baseboard 46 (shown in FIGS. 1-3 and 7), the wheelbase 74 being adjustable in width; a back wheel 76 located on the back end 50 of the wheel baseboard 46 (shown in FIGS. 1 and 4-7); an adjustable vertical pole 78 having a first end 80 and second end 82, the adjustable vertical pole 78 comprised of two pole parts 84, 84', in which one pole part 84 fits telescopically into the other pole part 84' (shown in FIGS. 1, 2 and 7) so that the length of the adjustable vertical pole 78 can be increased or decreased, the first end 80 of the adjustable vertical pole 78 connected to the central portion 28 of the handlebar 24, the second end 82 of the adjustable vertical pole 78 fitting into the seat circular opening 44 and the wheel baseboard circular opening 58.

Figure 2:
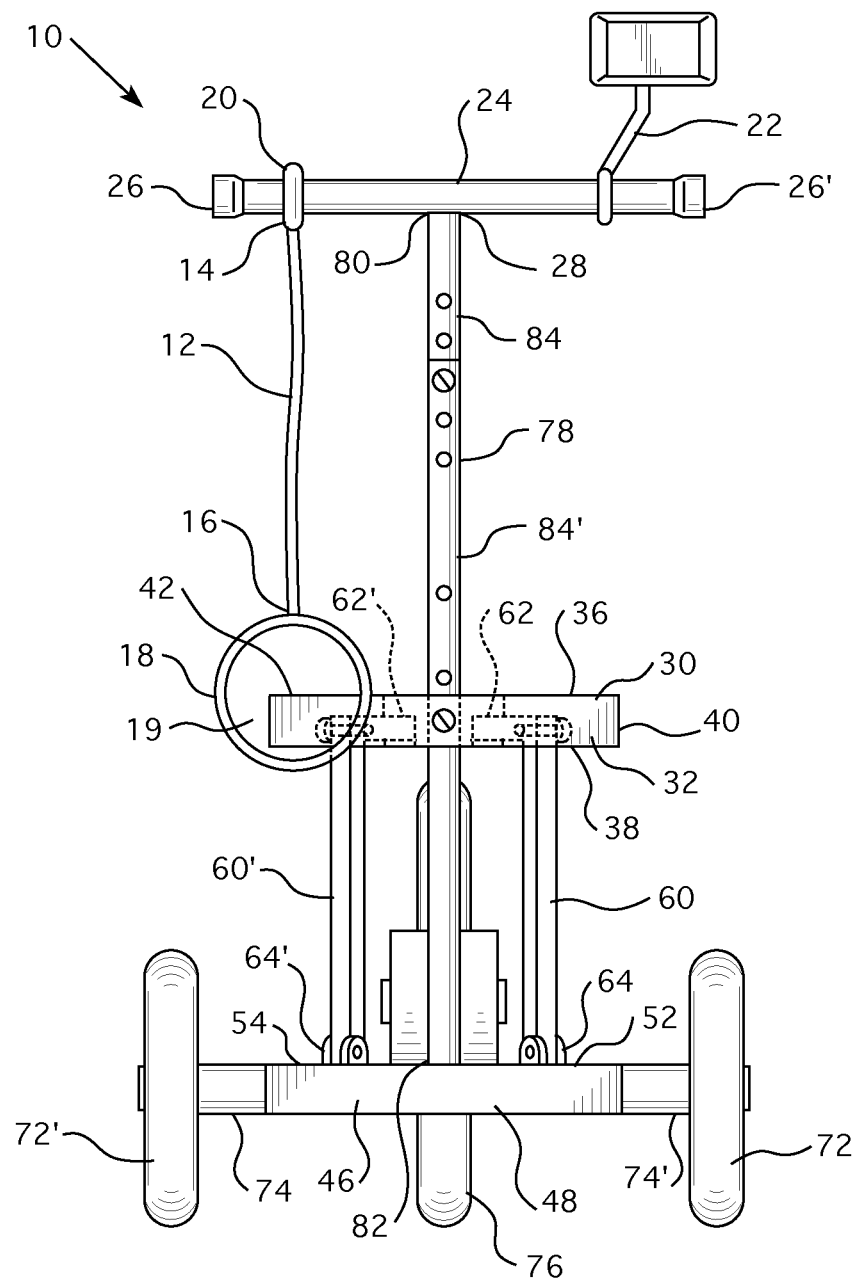
FIG. 2 is a front view of the medical ambulatory device, in accordance with an embodiment of the invention.
Figure 7:
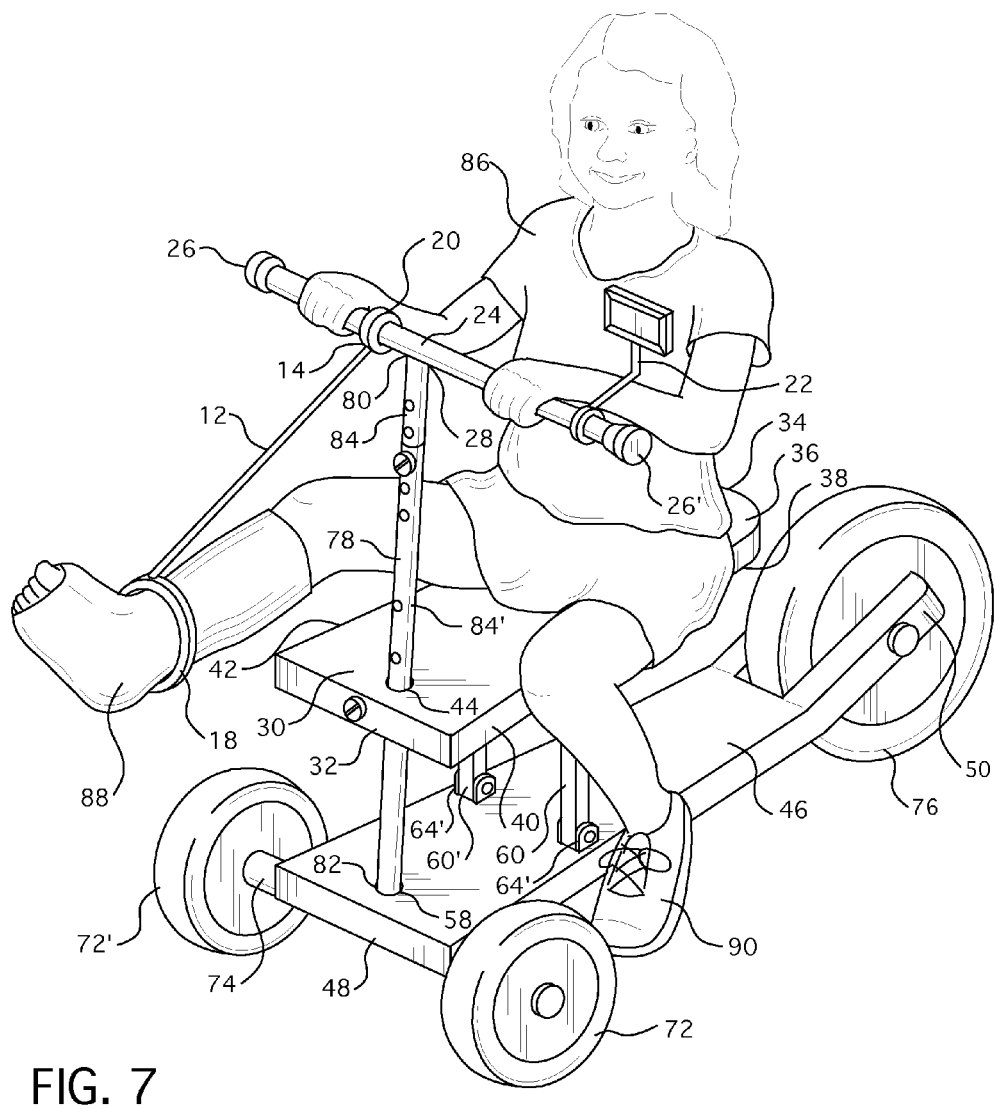
FIG. 7 is a perspective view of medical ambulatory device in use by a child, in which the right foot of the child is suspended in the air via the flexible, elastic harness, in accordance with an embodiment of the invention.

The medical ambulatory device 10 also includes a counterbalance weight 22 and a flexible, elastic structure 12, referred to herein as a "harness" 12 (shown best in FIGS. 1, 2 and 7). The harness 12 has a first end 14 and a second end 16. The first end 14 of the harness 12 terminates in a harness attachment means 20, and the second end 16 terminates in a circular ring 18 having an interior opening 19. The flexible, elastic structure of the harness 12 allows the circular ring 18 to expand or contract so that the circular ring 18 fits snugly and securely around an injured lower limb 88 of a child 86 (shown in FIG. 7). The device 10 also includes a counterbalance weight 22. The harness attachment means 20 is attached adjacent to the one end 26 of the handlebar 24, and the counterbalance weight 22 is attached adjacent to the other end 26' of the handlebar 24 (best shown in FIGS. 1, 2 and 7).

In accordance with the invention, the harness attachment means 20 includes a circular band that fits flexibly, snugly and reversibly over the handlebar 24.

In accordance with the invention, any suitable attachment means can be used for attachment to the first, second and third support bracket attachment means, so long as the attachment means allows for the reversible attachment of the first and second adjustable seat support brackets thereon.

Any suitable elastic, flexible material may be used to make the harness 12, including, without limitation, natural rubber, synthetic rubber or rubber composites.

In accordance with the invention, the adjustable vertical pole 78 can be adjusted in height by moving the pole parts 84, 84' inwardly or outwardly with each other so that the distance of the handlebar 24 from the top side 36 of the seat 30 ranges from between about 5 inches to about 15 inches. In an embodiment, the distance of the handlebar 24 from the top side 36 of the seat 30 is about 10 inches.

Figure 4:
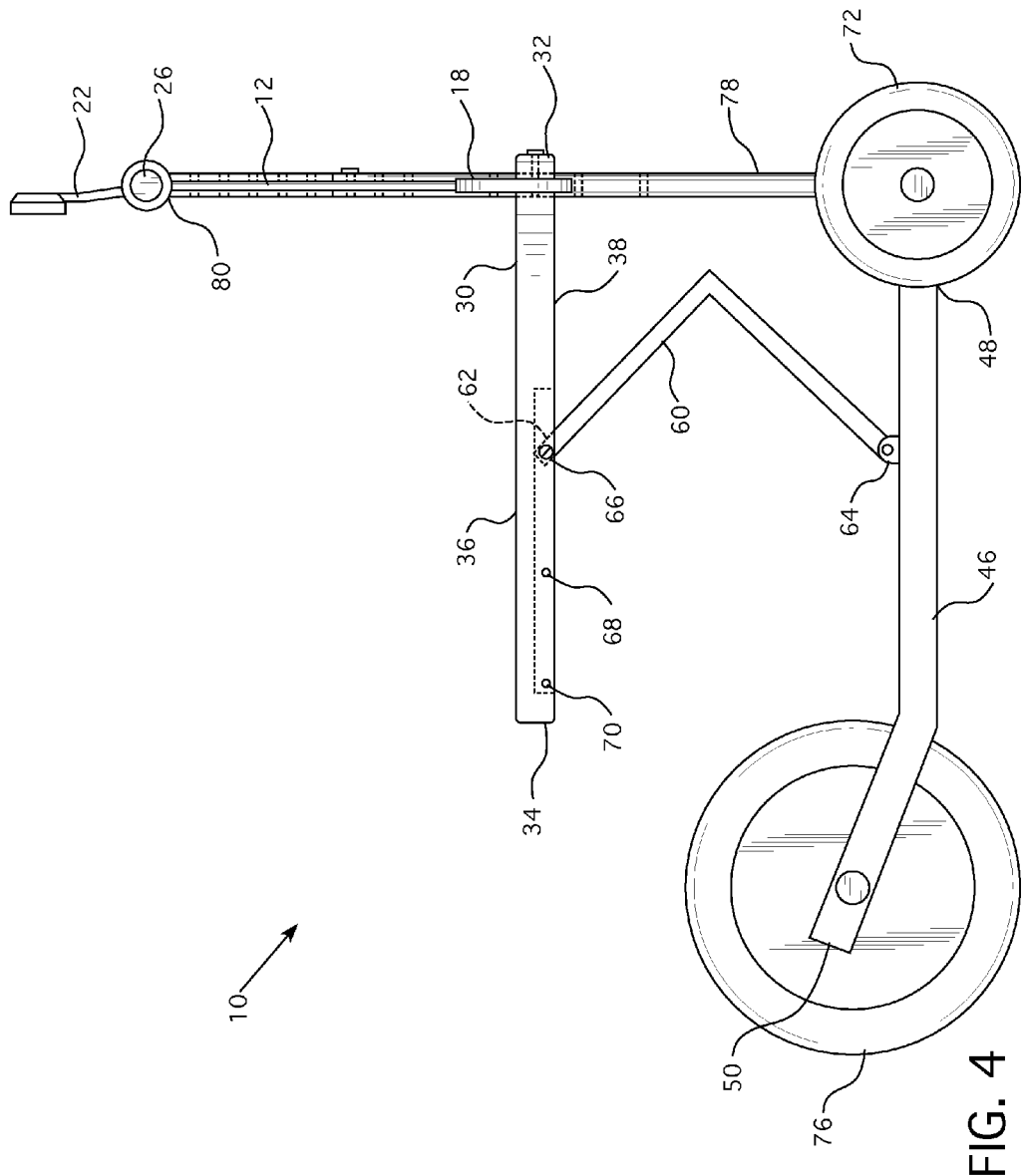
FIG. 4 is a side view of the medical ambulatory device showing the support brackets attached to the first support bracket attachment means of the seat to raise the seat to its highest position, in accordance with an embodiment of the invention.
Figure 5:
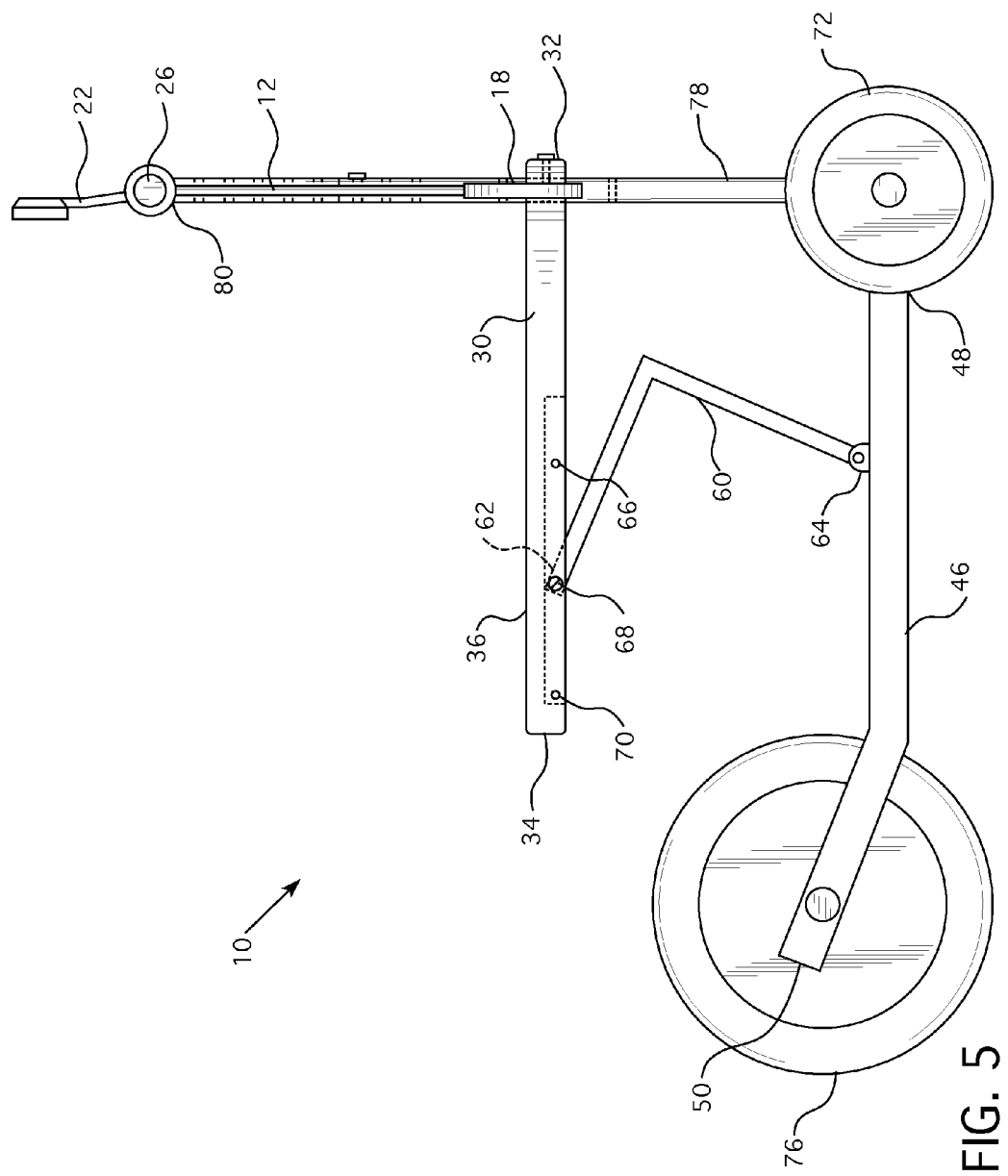
FIG. 5 is a side view of the medical ambulatory device showing the support brackets attached to the second support bracket attachment means of the seat to raise the seat to its intermediate position, in accordance with an embodiment of the invention.
Figure 6:
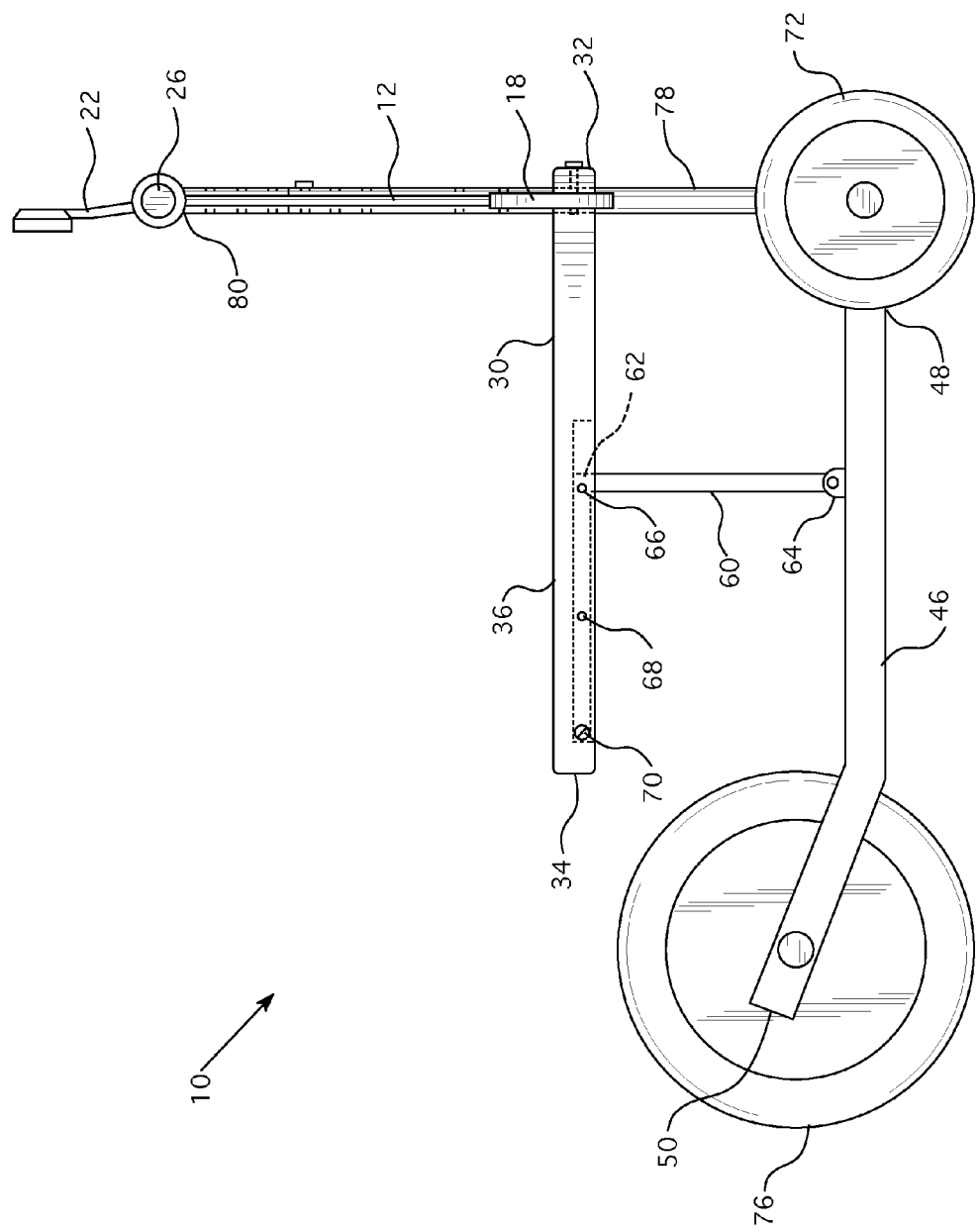
FIG. 6 is a side view of the medical ambulatory device showing the support brackets attached to the third support bracket attachment means of the seat to raise the seat to its lowest position, in accordance with an embodiment of the invention.

As shown in FIGS. 4-6, the first adjustable seat support bracket 60 and the second adjustable seat support bracket 60' each are L-shaped, with each arm of the L equal in length.

In accordance with the invention, the invention contemplates that the injured limb 90 may be encased in a cast, and thus the counterbalance weight 22 is placed on the handlebar 24 opposite to where the harness 12 is attached in order to balance the additional weight of the cast. Thus, a counterbalance weight that weighs substantially the same as the weight of the cast is placed on the handlebar. In an embodiment, the counterbalance weight weighs between one pound and 5 pounds. In an embodiment, the counterbalance weight 22 may be in the form of a rear-view mirror.

Figure 3:
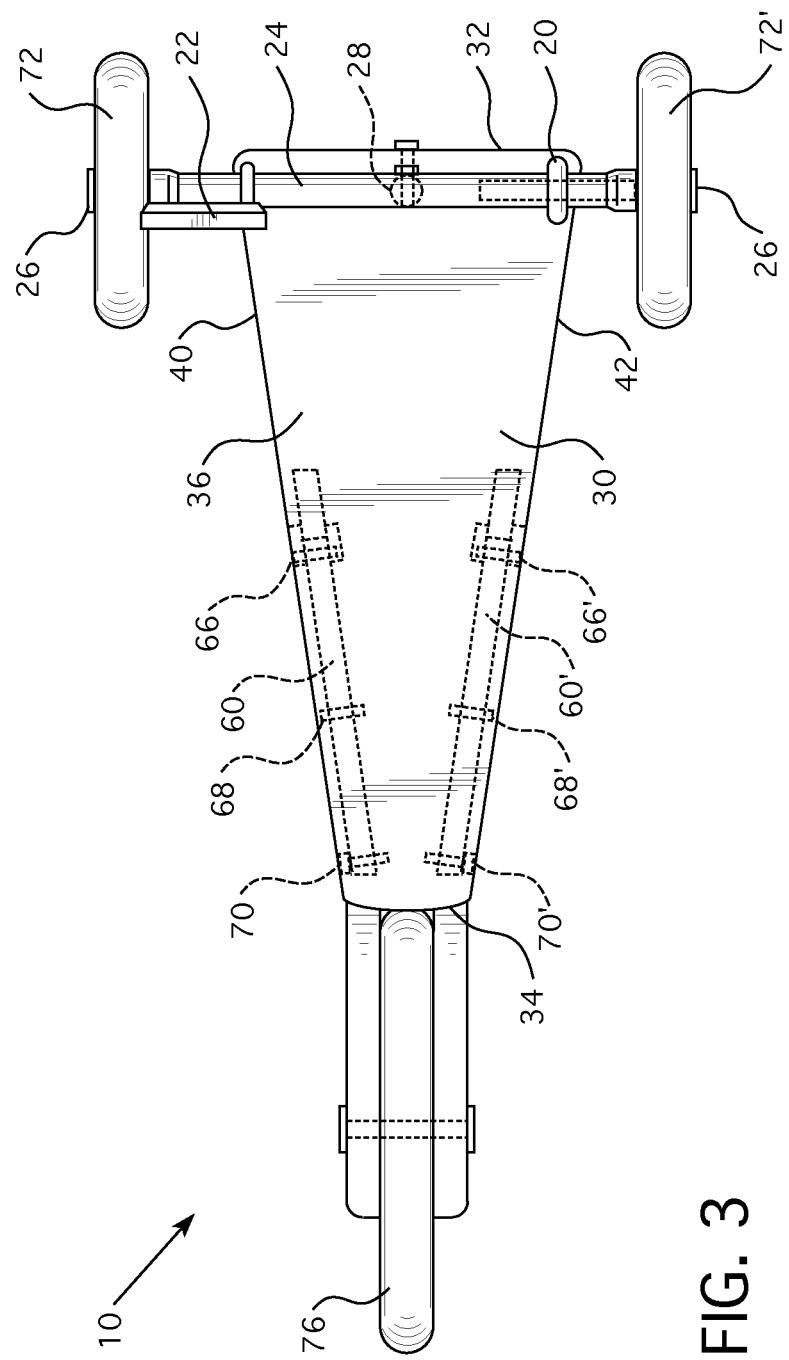
FIG. 3 is a top view of the medical ambulatory device, in accordance with an embodiment of the invention.

In accordance with the invention, the ambulatory vehicle has three different seat positions: a high position, an intermediate position, and a low position. As shown in FIGS. 3 and 4, the seat 30 is placed to its highest position by attaching the first adjustable seat support bracket 60 and the second adjustable seat support bracket 60' to the first support bracket attachment means of the first set 66 and the first support bracket attachment means of the second set 66', respectively; the seat 30 is placed to its intermediate position by attaching the first adjustable seat support bracket 60 and the second adjustable seat support bracket 60' to the second support bracket attachment means of the first set 68 and the second support bracket attachment means of the second set 68', respectively; and the seat 30 is placed to its lowest position by attaching the first adjustable seat support bracket 60 and the second adjustable seat support bracket 60' to the third support bracket attachment means of the first set 70 and the third support bracket attachment means of the second set 70', respectively.

In accordance with the invention, the distance between the seat 30 and the wheel baseboard 46 ranges between about 13 inches and about 16 inches when the seat is in its highest position. When the seat 30 is in its intermediate position, the distance between the seat 30 and the wheel baseboard 46 is between about 9 inches and about 12 inches. When the seat 30 is in its lowest position, the distance between the seat 30 and the wheel baseboard 46 is between 5 inches and 8 inches. In an embodiment, when the seat 30 is in its highest position, the distance between the seat 30 and the wheel baseboard 46 is about 14 inches; when the seat 30 is in its intermediate position, the distance between the seat 30 and the wheel baseboard 46 is about 10 inches; and when the seat 30 is in its lowest position, the distance between the seat 30 and the wheel baseboard 46 is about 6 inches.

In accordance with the invention, the maximum length of the adjustable vertical pole 78 is between about 20 inches and about 40 inches, and the minimum length is between about 10 inches and about 20 inches. In an embodiment, the maximum length of the adjustable vertical pole 78 is about 24 inches, and the minimum length is about 18 inches.

To ensure stability of the ambulatory device, the diameter of the back wheel 76 may be larger than the diameter of the first and second front wheels 72, 72' (shown in FIGS. 1 and 3-7). In addition, when the seat 30 is in its highest position, the wheelbase 74 may adjusted to a width of about 25 inches; when the seat 30 is in its intermediate position, the wheelbase may adjusted to a width of about 20 inches; and when the seat 30 is in its lowest position, the wheelbase may be is adjusted to a width of about 15 inches.

Referring now to FIG. 7, the method of use of the ambulatory device comprises adjusting the height of the handlebar 24 and seat 30 of the ambulation vehicle to a height that is substantially the height that is eye-level of a child 86 using the device when the child 86 is standing; adjusting the width of the wheelbase 74 to provide optimal stability; placing the flexible, elastic ring-shaped harness 12 on the side of the handlebar 24 that is the same side of an injured lower limb 88 of the child 86, and placing the counterbalance weight 22 on the other side of the handlebar 24; placing the child 86 on the seat 30 of the ambulation vehicle; having the child 86 grasp the handlebar 24 with their hands; placing the foot of the injured lower limb 88 of the child 86 through the harness 12 so that the injured lower limb 88 is suspended in the air in a substantially elevated position; and moving the ambulation vehicle by having the child 86 repeatedly push back on the ground with their uninjured lower limb 90 in order to propel the ambulation vehicle forward.

To provide stability to the ambulatory device, when the injured lower limb is in a cast, a counterbalance weight 22 is selected that weighs substantially the same as the weight of the cast on the child.

While the invention has been particularly shown and described with reference to embodiments described above, it will be understood by those skilled in the art that various alterations in form and detail may be made therein without departing from the spirit and scope of the invention, as defined by the appended claims.

What is claimed is:

1. A medical ambulatory device for children, comprising:
    a flexible, elastic harness, said harness having a first end and second end, said first end having a harness attachment means, said second end terminating in a circular ring having an interior opening, said circular ring capable of expanding or contracting to fit securely around an injured lower limb of a child;
    a counterbalance weight; and
    an ambulation vehicle, comprising:
        a handlebar having two ends and a central portion;
        a seat having a front end, a back end, a top side, a bottom side, a first side and a second side, said front end having a circular opening therein, and said bottom side having two sets of a first support bracket attachment means, a second support bracket attachment means and a third support bracket attachment means, said first set located adjacent to the first side of the seat, and said second set located adjacent to the second side of the seat, said first, second and third support bracket attachment means spaced evenly apart;
        a wheel baseboard having a front end, a back end, a first side, a second side and a central portion, said front end having a circular opening therein;
        a first adjustable seat support bracket and a second adjustable seat support bracket, each adjustable seat support bracket having a first end and a second end, said first end of said first adjustable seat support bracket reversibly attached to the first, second or third support attachment means of the first set, and said second end of said first adjustable seat support bracket connected to the central portion adjacent to the first side of the wheel baseboard, and said first end of said second adjustable support bracket is reversibly attached to the first, second or third attachment means of the second set, and said second end of said second adjustable seat support bracket connected to the central portion adjacent to the second side of the wheel baseboard;
        a first front wheel and a second front wheel connected to a wheelbase located at the front end of the wheel baseboard, said wheel baseboard adjustable in width;
        a back wheel located on the back end of the wheel baseboard;
        an adjustable vertical pole having a first end and second end, said adjustable vertical pole comprised of two pole parts in which one pole part fits telescopically into the other pole part so that the length of the adjustable vertical pole can be increased or decreased, said first end of the adjustable vertical pole connected to the central portion of the handlebar, said second end of the adjustable vertical pole fitting into the seat circular opening and the wheel baseboard circular opening,
    wherein said harness attachment means is attached adjacent to the one end of said handlebar, and wherein the counterbalance weight is attached adjacent to the other end of the handlebar.

2. The medical ambulatory device for children of claim 1, wherein the first adjustable seat support bracket and the second adjustable seat support bracket each are L-shaped with each arm of the L equal in length.

3. The medical ambulatory device for children of claim 1, wherein the length of the vertical pole can be adjusted so that the handlebar ranges from about 5.0 inches to about 15 inches above the top side of the seat.

4. The medical ambulatory device for children of claim 3, wherein the length of the vertical pole is adjusted so that the handlebar is about 10.0 inches above the top side of the seat.

5. The medical ambulatory device for children of claim 1, wherein the first adjustable seat support bracket and the second adjustable seat support bracket are reversibly attached to the first support bracket attachment means of the first set and the second set, respectively, to place the seat to its highest position.

6. The medical ambulatory device for children of claim 1, wherein the first adjustable seat support bracket and the second adjustable support bracket are reversibly attached to the second support bracket attachment means of the first set and the second set, respectively, to place the seat to its intermediate position.

7. The medical ambulatory device for children of claim 5, wherein the first adjustable seat support bracket and the second adjustable seat support bracket are reversibly attached to the third support bracket attachment means of the third set, respectively, to place the seat to its lowest position.

8. The medical ambulatory device for children of claim 5, wherein the distance between the seat and the wheel baseboard is between about 13 inches and about 16 inches when the seat is in its highest position.

9. The medical ambulatory device for children of claim 6, wherein the distance between the seat and the wheel baseboard is between about 9 inches and about 12 inches when the seat is in its intermediate position.

10. The medical ambulatory device for children of claim 7, wherein the distance between the seat and the wheel baseboard is between about 5 inches and about 8 inches when the seat is in its lowest position.

11. The medical ambulatory device for children of claim 5, wherein when the seat is in its highest position, the wheelbase is adjusted to a width of about 25 inches.

12. The medical ambulatory device for children of claim 6, wherein when the seat is in the intermediate position, the wheelbase is adjusted to a width of about 20 inches.

13. The medical ambulatory device for children of claim 7, wherein when the seat is in its lowest position, the wheelbase is adjusted to a width of about 15 inches.

14. The medical ambulatory device for children of claim 1, wherein the maximum length of the vertical pole is between about 20 inches and about 40 inches, and the minimum length is between about 10 inches and about 20 inches.

15. The medical ambulatory device for children of claim 14, wherein the maximum length of the vertical pole is about 24 inches, and the minimum length is about 18 inches.

16. The medical ambulatory device for children of claim 1, wherein the diameter of the back wheel is larger than the diameter of the first front wheel and the second front wheel.

17. The medical ambulatory device for children, wherein the counterbalance weight has a weight that is between about one pound and 5 pounds.

18. The medical ambulatory device for children, wherein the counterbalance weight is a rear-view mirror.

19. A method of ambulation for a child having an injured leg, ankle or foot, the method comprising:
having a child use the medical ambulatory device of claim 1 by:
adjusting the height of the handlebar and seat of the ambulation vehicle as claimed in claim 1 to a height that is substantially the height that is eye-level of the child when the child is standing;
adjusting the width of the wheelbase to provide optimal stability;
placing the flexible, elastic ring-shaped harness on the side of the handlebar that is the same side of the injured lower limb of the child, and placing the counterbalance weight on the other side of the handlebar;
placing the child on the seat of the ambulation vehicle;
having the child grasp the handlebar with their hands;
placing the foot of the injured limb of the child through the harness so that the injured lower limb is suspended in the air in a substantially elevated position; and
moving the ambulation vehicle by having the child repeatedly push back on the ground with their uninjured lower limb in order to propel the ambulation vehicle forward.

20. The method of claim 19, wherein when the injured leg, ankle or foot is in a cast, the counterbalance weight weighs substantially the same as the weight of the cast.

* * * * *